(12) United States Patent
Moore et al.

(10) Patent No.: US 10,512,785 B2
(45) Date of Patent: Dec. 24, 2019

(54) IMPLANTABLE WIRELESS ACCOUSTIC STIMULATORS WITH HIGH ENERGY CONVERSION EFFICIENCIES

(71) Applicant: EBR Systems, Inc., Sunnyvale, CA (US)

(72) Inventors: David F. Moore, San Carlos, CA (US); Paul Mohr, Aptos, CA (US); N. Parker Willis, Atherton, CA (US); Axel F. Brisken, Fremont, CA (US)

(73) Assignee: EBR Systems, Inc., Sunnyvale, CA (US)

( * ) Notice: Subject to any disclaimer, the term of this patent is extended or adjusted under 35 U.S.C. 154(b) by 0 days.

(21) Appl. No.: 16/250,943

(22) Filed: Jan. 17, 2019

(65) Prior Publication Data

US 2019/0151667 A1  May 23, 2019

Related U.S. Application Data

(60) Continuation of application No. 16/051,338, filed on Jul. 31, 2018, which is a continuation of application (Continued)

(51) Int. Cl.
*A61N 1/378* (2006.01)
*A61N 1/375* (2006.01)
(Continued)

(52) U.S. Cl.
CPC .............. *A61N 1/3787* (2013.01); *A61N 1/02* (2013.01); *A61N 1/05* (2013.01); *A61N 1/362* (2013.01);
(Continued)

(58) Field of Classification Search
None
See application file for complete search history.

(56) References Cited

U.S. PATENT DOCUMENTS 3,659,615 A  5/1972  Enger
3,735,756 A  5/1973  Richards
(Continued)

FOREIGN PATENT DOCUMENTS

DE   4330680 A1   3/1995
GB   1146976 A    3/1969
(Continued)

OTHER PUBLICATIONS

European office action dated Apr. 13, 2012 for Application No. 09725884.2.
(Continued)

*Primary Examiner* — Kennedy Schaetzle
(74) *Attorney, Agent, or Firm* — Perkins Coie LLP

(57) ABSTRACT

A controller-transmitter transmits acoustic energy through the body to an implanted acoustic receiver-stimulator. The receiver-stimulator converts the acoustic energy into electrical energy and delivers the electrical energy to tissue using an electrode assembly. The receiver-stimulator limits the output voltage delivered to the tissue to a predetermined maximum output voltage. In the presence of interfering acoustic energy sources output voltages are thereby limited prior to being delivered to the tissue.

Furthermore, the controller-transmitter estimates the output voltage that is delivered to the tissue by the implanted receiver-stimulator. The controller-transmitter measures a query spike voltage resulting from the electrical energy delivered to the tissue by the receiver-stimulator, and computes a ratio of the predetermined maximum output voltage and a maximum query spike voltage. The maximum query spike voltage is computed by detecting a query spike voltage plateau. Based on this ratio, the controller-transmitter uses a measured query spike voltage to estimate the output voltage delivered by the receiver-stimulator to tissue.

8 Claims, 12 Drawing Sheets

Related U.S. Application Data

No. 15/138,046, filed on Apr. 25, 2016, now Pat. No. 10,052,493, which is a continuation of application No. 14/883,925, filed on Oct. 15, 2015, now Pat. No. 9,343,654, which is a division of application No. 14/059,228, filed on Oct. 21, 2013, now Pat. No. 9,180,285, which is a division of application No. 13/734,680, filed on Jan. 4, 2013, now Pat. No. 8,588,926, which is a continuation-in-part of application No. 12/721,483, filed on Mar. 10, 2010, now Pat. No. 8,364,276.

(51) Int. Cl.
| | | |
|---|---|---|
| *H01L 41/113* | (2006.01) | |
| *H02N 2/18* | (2006.01) | |
| *A61N 1/02* | (2006.01) | |
| *H01L 41/25* | (2013.01) | |
| *A61N 1/362* | (2006.01) | |
| *A61N 1/372* | (2006.01) | |
| *A61N 1/05* | (2006.01) | |

(52) U.S. Cl.
CPC ......... *A61N 1/3756* (2013.01); *A61N 1/3758* (2013.01); *A61N 1/37205* (2013.01); *H01L 41/113* (2013.01); *H01L 41/25* (2013.01); *H02N 2/181* (2013.01); *H02N 2/186* (2013.01); *H02N 2/188* (2013.01); *A61B 2560/0214* (2013.01); *Y10T 29/42* (2015.01)

(56) References Cited

U.S. PATENT DOCUMENTS

| | | | |
|---|---|---|---|
| 3,767,971 | A | 10/1973 | Patrick, Jr. |
| 4,050,004 | A | 9/1977 | Greatbatch |
| 5,193,539 | A | 3/1993 | Schulman |
| 5,266,746 | A | 11/1993 | Nishihara |
| 5,314,453 | A | 5/1994 | Jeutter |
| 5,545,183 | A | 8/1996 | Altman |
| 5,749,909 | A | 5/1998 | Schroeppel et al. |
| 5,833,710 | A | 11/1998 | Jacobson |
| 6,140,740 | A | 10/2000 | Porat |
| 6,327,498 | B1 | 12/2001 | Kroll |
| 6,504,286 | B1 | 1/2003 | Porat |
| 6,628,989 | B1 | 9/2003 | Penner |
| 6,654,638 | B1 | 11/2003 | Sweeney |
| 6,764,446 | B2 | 7/2004 | Wolinsky |
| 6,771,785 | B2 | 8/2004 | Pompei |
| 7,283,874 | B2 | 10/2007 | Penner |
| 7,489,967 | B2 | 2/2009 | Von Arx et al. |
| 7,522,962 | B1 | 4/2009 | Doron et al. |
| 7,542,804 | B2 | 6/2009 | Mandell |
| 7,606,621 | B2 | 10/2009 | Brisken |
| 7,610,092 | B2 | 10/2009 | Cowan et al. |
| 7,865,247 | B2 | 1/2011 | Smith |
| 7,983,748 | B2 | 7/2011 | Ruse |
| 8,369,960 | B2 * | 2/2013 | Tran ..................... A61N 1/3787 607/30 |
| 8,588,926 | B2 | 11/2013 | Moore et al. |
| 9,180,285 | B2 | 11/2015 | Moore |
| 9,343,654 | B2 | 5/2016 | Moore |
| 9,731,138 | B1 | 8/2017 | Stadler |
| 9,981,138 | B2 | 5/2018 | Willis |
| 10,052,493 | B2 | 8/2018 | Moore et al. |
| 2002/0077673 | A1 | 6/2002 | Penner |
| 2003/0104269 | A1 | 6/2003 | Gan et al. |
| 2004/0172083 | A1 | 9/2004 | Penner |
| 2004/0204744 | A1 | 10/2004 | Penner |
| 2005/0154294 | A1 | 7/2005 | Uchiyama |
| 2005/0165456 | A1 | 7/2005 | Mann |
| 2006/0004424 | A1 | 1/2006 | Loeb et al. |
| 2006/0136004 | A1 * | 6/2006 | Cowan ............... A61N 1/37205 607/33 |
| 2006/0136005 | A1 | 6/2006 | Brisken |
| 2007/0027580 | A1 | 2/2007 | Cowan et al. |
| 2007/0055184 | A1 | 3/2007 | Echt et al. |
| 2007/0167988 | A1 | 7/2007 | Cernasov |
| 2007/0233200 | A1 | 10/2007 | Maschke |
| 2007/0282383 | A1 | 12/2007 | Koyama |
| 2007/0293895 | A1 | 12/2007 | Cowan |
| 2008/0243210 | A1 | 10/2008 | Doron et al. |
| 2008/0269818 | A1 | 10/2008 | Sullivan |
| 2008/0294208 | A1 | 11/2008 | Willia |
| 2008/0312720 | A1 * | 12/2008 | Tran ..................... A61N 1/3787 607/61 |
| 2010/0234924 | A1 * | 9/2010 | Willis ................. A61N 1/3787 607/63 |
| 2012/0203306 | A1 | 8/2012 | Sarvazyan |
| 2018/0345026 | A1 | 12/2018 | Moore |

FOREIGN PATENT DOCUMENTS

| | | |
|---|---|---|
| WO | 2005009535 A1 | 2/2005 |
| WO | 2007016581 A2 | 2/2007 |
| WO | 2007016581 A3 | 5/2007 |
| WO | 2007149936 A2 | 12/2007 |
| WO | 2007149936 A3 | 10/2008 |
| WO | 2009120785 A2 | 10/2009 |
| WO | 2009120785 A3 | 12/2009 |
| WO | 2011112865 A1 | 9/2011 |

OTHER PUBLICATIONS

European search report and opinion dated Jun. 27, 2011 for EP Application No. 09725884.2.
European search report and opinion dated Sep. 26, 2013 for EP Application No. 11754116.9.
European search report dated Apr. 18, 2012 for Application No. 12151794.0.
Final Office Action dated Dec. 22, 2014 in U.S. Application No. 13/648,027 for Willis, filed Oct. 9, 2012, 7 pages.
International search report and written opinion dated May 19, 2011 for PCT/US2011/027985.
International search report and written opinion dated May 25, 2009 for PCT/US2009/038258.
Non-Final Office action dated Jan. 12, 2015 for U.S. Appl. No. 14/059,228.
Non-Final Office Action dated Jun. 11, 2012 in U.S. Appl. No. 12/721,483 for Willis, filed Mar. 10, 2010, 8 pages.
Non-Final Office Action dated Jun. 13, 2014 in U.S. Appl. No. 13/648,027 for Willis, filed Oct. 9, 2012, 9 pages.
Notice of allowance dated Jul. 22, 2013 for U.S. Appl. No. 13/734,680.
Notice of allowance dated Jul. 31, 2015 for U.S. Appl. No. 14/059,228.
Notice of allowance dated Sep. 28, 2012 for U.S. Appl. No. 12/721,483.
Notice of Allowance dated Jan. 20, 2016 in U.S. Appl. No. 14/883,925 for Moore, filed Oct. 15, 2015, 9 pages.
Notice of Allowance dated Jan. 30, 2018 in U.S. Appl. No. 13/648,027 for Willis, filed Oct. 9, 2012, 5 pages.
Notice of Allowance dated Jul. 22, 2013 in U.S. Appl. No. 13/734,680 for Moore, filed Jan. 4, 2013, 10 pages.
Notice of Allowance dated Sep. 26, 2012 in U.S. Appl. No. 12/721,483 for Willis, filed Mar. 10, 2010, 5 pages.
Non-Final Office Action dated Aug. 24, 2017 in U.S. Appl. No. 15/138,046 for Moore, filed Apr. 25, 2016, 16 pages.
Notice of Allowance dated Apr. 18, 2018 in U.S. Appl. No. 15/138,046 for Moore, filed Apr. 25, 2016, 5 pages.

* cited by examiner

IMPLANTABLE WIRELESS ACCOUSTIC STIMULATORS WITH HIGH ENERGY CONVERSION EFFICIENCIES

CROSS-REFERENCES TO RELATED APPLICATIONS

This application is a continuation-in-part of International (PCT) Patent Application No. PCT/US2009/038258, filed Mar. 25, 2009, which claimed the benefit of U.S. Provisional Patent Application No. 61/039,340, filed on Mar. 25, 2008, the disclosures of which are incorporated herein by reference.

BACKGROUND OF THE INVENTION

1. Field of Invention

This invention relates generally to wireless acoustic stimulation systems, devices, and methods for stimulating biological tissue and, in particular, for a receiver-stimulator that converts acoustic energy received from a controller-transmitter into electrical energy, and delivers the electrical energy to the tissue at a level that does not stimulate tissue during diagnostic echocardiography. Furthermore, this invention relates to a controller-transmitter that can determine the electrical energy output by a receiver-stimulator.

2. Description of the Background Art

Stimulation of cardiac tissue can be achieved using acoustic energy based systems comprising a controller-transmitter and one or more implanted receiver-stimulator devices. The controller-transmitter transmits acoustic energy by producing an acoustic field that is transmitted over time. The acoustic field is a propagating acoustic wave defined by its direction and its intensity (i.e., its power per unit area, typically expressed as $W/m^2$). The acoustic field varies and attenuates as it propagates through the body due to absorption, refraction, and reflection. To minimize losses, the controller-transmitter focuses, or attempts to maximize, the acoustic field on the receiver-stimulator. In turn, the receiver-stimulator maximizes harvesting and converting of the acoustic field impinging upon it into electrical power delivered over time to the tissue to stimulate the tissue (stimulation energy). In general, this receiver-stimulator is a specialized transducer, that is, a device that converts acoustic energy to electrical energy. In another perspective the receiver-stimulator uses the converted energy as a tissue stimulator that delivers electrical energy to cardiac or other tissue through tissue stimulation electrodes. The controller-transmitter may be applied externally on the body, but will usually be implanted in the body, requiring that the controller-transmitter have a reasonable size, similar to that of implantable pacemakers, and that the controller-transmitter be capable of operating from batteries for a lengthy period, typically three or more years. Thus, a chronically implanted acoustic wireless stimulation system that uses ultrasound to transfer pacing energy requires all aspects of the system to be as energy efficient as possible to increase the service life of the device and additionally reduce the battery size.

Furthermore, it is also conceivable that a recipient of the implanted acoustic wireless stimulation system may be exposed to environments with interfering acoustic fields, such as acoustic fields generated by diagnostic ultrasound imaging devices. Interference, defined as inadvertent pacing/stimulation from diagnostic imaging systems, is a particular concern when designing a wireless system that maximizes acoustic to electrical energy conversion efficiency. The FDA guidance on diagnostic ultrasound imaging (2008) provides the following acoustic output limits for track 1 devices (track 1 devices do not require specific labeling for large acoustic output):

TABLE 1

| Use | $I_{SPTA.3}$ (mW/cm²) | $I_{SPPA.3}$ (W/cm²) | or MI |
|---|---|---|---|
| Peripheral Vessel | 720 | 190 | 1.9 |
| Cardiac | 430 | 190 | 1.9 |
| Fetal Imaging & Other* | 94 | 190 | 1.9 |
| Ophthalmic | 17 | 28 | 0.23 |

The relevant limit of concern to the present invention is the ISPPA limit which is presented as the acoustic intensity averaged over a single imaging pulse taken at the spatial peak of the field. The spatial peak is the point in space where the largest acoustic field is produced. According to table 1, the acoustic output limit for a track 1 diagnostic device is 190 W/cm² (1.9E6 W/m²). A typical acoustic field required to pace the heart with the implanted receiver-stimulator would be on the order of 170 W/m², which is 11,000 times smaller than the track 1 diagnostic device limit of 1.9E6 W/m². In the context of the wireless stimulator, this implies that imaging devices will be producing acoustic fields that are very large (four orders of magnitude larger) than those required to stimulate cardiac tissue.

In addition to the strength of the acoustic fields, the operation frequency and duration of pulses used in diagnostic imaging must also be taken into account to determine any potential acoustic interference from diagnostic devices.

Most diagnostic imaging systems operate within the frequency range of 2-10 MHz, whereas the typical operating frequency for an implanted acoustic wireless system is within the range of 800 kHz to 1.3 MHz. Although most diagnostic imaging systems operate at higher frequencies than the implanted acoustic wireless system, state of the art systems can operate in a harmonic imaging mode where transmission occurs at a lower frequency and reception intentionally occurs at a harmonic multiple of the transmit frequency. For example, the Phillips system transmits at 1.2 MHz but receives at 2.4 MHz. It is also known that some diagnostic imaging systems in use today can operate at as low as 500 KHz in the harmonic imaging mode. Therefore, it is reasonable to assume that at least some diagnostic imaging systems operate with sufficient acoustic intensity and within a frequency range that may interfere with the operation of implantable acoustic stimulation systems without any safeguard measures.

To achieve optimal stimulation energy efficiency, an implanted acoustic wireless stimulation system should receive acoustic energy at a pulse-width within the range of 0.2-1.0 ms. Pulses that are shorter or longer than the optimal range require more stimulation energy than a pulse that is within the optimal range.

FIG. 1 illustrates the electrical energy needed to stimulate the tissue at different pulse widths taken at different times during an acute procedure. The electrical energy required for sufficient pacing for the shortest duration pulse (0.02 msec=20 μsec) shown in FIG. 1 is 5-10 times greater than the minimum electrical energy required for an optimal pulse width of 500 μsec. The longest duration pulses used in diagnostic imaging are those used for Doppler modes and they can be up to 8 μsec long (for the purposes of illustration, duration pulses used in diagnostic imaging are approximated as 10 μsec long), which is reasonably close to the 20 μsec data points in the curves shown in FIG. 1. Taking into consideration that the duration is reduced from 20 μsec down to 10 μsec, it is reasonable then to infer that pulse widths used in diagnostic imaging would require approximately 20 times more converted acoustic energy to pace tissue than the converted acoustic energy of the optimal pulse widths used for wireless pacing. However the acoustic energy must be compressed into a 10 μsec pulse rather than the optimal pulse of 500 μsec. Therefore, the acoustic intensity required to stimulate the tissue with a short duration 10 μsec must be $$\frac{20 \cdot 500 \text{ μsec}}{10 \text{ μsec}} = 1,000$$

times greater than that is required to stimulate with a 500 μsec pulse. This is three orders of magnitude, but is still insufficient protection as it does not provide the four orders of magnitude discussed previously that would be required to ensure that interference from diagnostic imaging sources does not stimulate cardiac tissue. Clearly, without some additional measures an implanted acoustic wireless stimulation system cannot be both optimally energy efficient by using the optimal pulse-width and immune to undesired stimulation in the presence of interfering acoustic fields such as those generated by diagnostic imaging equipment.

It would be desirable to provide implantable receiver devices which are able to function safely in the presence of interfering acoustic fields by limiting the converted electrical energy delivered to the tissue to a level that prevents undesired stimulation caused by any interfering acoustic fields.

The following patents and patent publications describe various wireless implantable stimulation systems: U.S. Pat. No. 7,283,874; U.S. Patent Publication Nos. 20070282383A1 and 20070233200A1. U.S. Pat. No. 7,283,874 by Penner et al. describes an implantable stimulation system that transmits acoustic waves to an implantable stimulator, and the implantable stimulator transforms the acoustic energy into electrical energy. The patent discloses using a voltage protector to prevent the energy storage device from overcharging, however the patent does not address preventing undesired stimulation due to acoustic interference from, say, an imaging system.

Historically, the very large body of knowledge associated with the assessment of cardiac tissue stimulation is based on delivery of electrical energy through electrodes of a wire/lead based system. The amount of energy required to stimulate tissue, referred to as the threshold, is affected by several typical system factors, e.g. electrode surface area, current density at the electrode-tissue interface, distance of an electrode from excitable tissue, etc. The threshold is expressed in electrical terms. Stimulation threshold is achieved when sufficient amplitude (voltage) delivered for sufficient time (pulse width) through an electrode-tissue interface (impedance) activates/stimulates tissue (capture). Practitioners of cardiac pacing identify the stimulation threshold for several practical reasons. One reason is to ensure that the pacing electrode is in proximity of excitable/viable tissue in order to select a suitable implant location and in order to use a reasonable energy level from a battery-based pacing system, a pacemaker. A low stimulation threshold, for example 1 Volt at 0.5 ms, would indicate that the electrode location would be adequate for acute and chronic pacing. Another reason that the stimulation threshold is identified is so that pacing systems can be programmed to output voltages and pulse width durations that exceed the threshold by a safety factor. Typically a 2-3 times threshold is used as the selected/programmed settings in a pacemaker. With this knowledge base in wide historic usage, it is highly desirable to be able to quantify the electrical energy being delivered to tissue by a wireless pacing system.

Current wireless implantable stimulation systems are unable to detect or measure the pacing voltage that is actually applied to the tissue, because there is no direct electrical connection to the implantable receiver electrode. Therefore, it would also be desirable to provide systems, devices and methods to infer the pacing voltage applied to the tissue in wireless implantable stimulation systems. It would also be desirable to have the implantable receiver devices limit the electrical energy output to a level that prevents interference from diagnostic acoustic sources. At least some of these objectives will be met by the inventions described hereinafter.

BRIEF SUMMARY OF THE INVENTION

The present embodiments provide wireless systems, devices, and methods for safely stimulating tissue by limiting the electrical output voltage to a level that does not stimulate tissue during diagnostic echocardiography. The present embodiments also disclose systems, devices, and methods configured to remotely estimate the output voltage delivered by a receiver-stimulator to the tissue.

In one aspect, a receiver-stimulator is configured to limit the output voltage that it delivers to tissue. Specifically, a controller-transmitter device transmits acoustic energy through the body to an implanted acoustic receiver-stimulator. The receiver-stimulator converts the acoustic energy into electrical energy and delivers the electrical energy to tissue using an electrode assembly. The receiver-stimulator is configured to limit the output voltage delivered to the tissue to a predetermined maximum output voltage, using a voltage limiter. As a result, output voltages delivered to the tissue due to interfering acoustic energy sources, such as diagnostic imaging systems, are limited to a level that does not stimulate tissue.

The voltage limiter in the receiver-stimulator may comprise a Zener diode or forward biased diodes. The receiver-stimulator may comprise a low pass filter to eliminate acoustic energy outside of the desired frequency range transmitted by the controller-transmitter.

In another aspect, a controller-transmitter is configured to estimate the output voltage that is delivered to the tissue by an implanted receiver-stimulator. The controller-transmitter transmits acoustic energy to the implanted receiver-stimulator which converts the acoustic energy into electrical energy and delivers the electrical to tissue using an electrode assembly. The receiver-stimulator is configured to limit the output voltage delivered to the tissue to a predetermined maximum output voltage. To estimate the output voltage of the receiver-stimulator, the controller-transmitter measures a query spike voltage resulting from the electrical energy delivered to the tissue by the receiver-stimulator. The controller-transmitter determines a maximum query spike voltage, for example by detecting a query spike voltage plateau, and computes a ratio of the predetermined maximum output voltage and the maximum query spike voltage. Once this ratio is computed, the controller-transmitter may use the ratio and a measured query spike voltage to estimate output voltages delivered by the receiver-stimulator to tissue. The controller-transmitter may be implanted in the body or external to the body. Further embodiments and variations are described in the detailed description below.

BRIEF DESCRIPTION OF THE DRAWINGS

The invention has other advantages and features which will be more readily apparent from the following detailed description of the invention and the appended claims, when taken in conjunction with the accompanying drawings, in which:

DETAILED DESCRIPTION OF THE INVENTION

Although the detailed description contains many specifics, these should not be construed as limiting the scope of the invention but merely as illustrating different examples and aspects of the invention. It should be appreciated that the scope of the invention includes other embodiments not discussed in detail. Various other modifications, changes and variations which will be apparent to those skilled in the art may be made in the arrangement, operation and details of the method and apparatus of the present invention disclosed herein without departing from the spirit and scope of the invention as described here.

The present invention generally provides wireless stimulation systems, devices, and methods that stimulate tissue by harvesting acoustic energy transmitted into the tissue and converting the acoustic energy into electrical energy which is then delivered to the tissue. Specifically, the present invention provides wireless systems, devices, and methods configured to operate safely by limiting the output voltage to a level that does not stimulate tissue during diagnostic echocardiography. Further embodiments disclose systems, devices, and methods configured to estimate the output voltage delivered by a receiver-stimulator to the tissue.

In a first aspect, the present invention provides an implantable receiver-stimulator device which is capable of wirelessly harvesting acoustic energy from an acoustic field delivered by an acoustic source such as an implantable controller-transmitter. The implantable receiver-transmitter converts the acoustic energy to electrical energy, and limits the output voltage to a level that does not stimulate tissue during diagnostic echocardiography, before delivering the electrical energy to the tissue using an electrode assembly.

Figure 1:
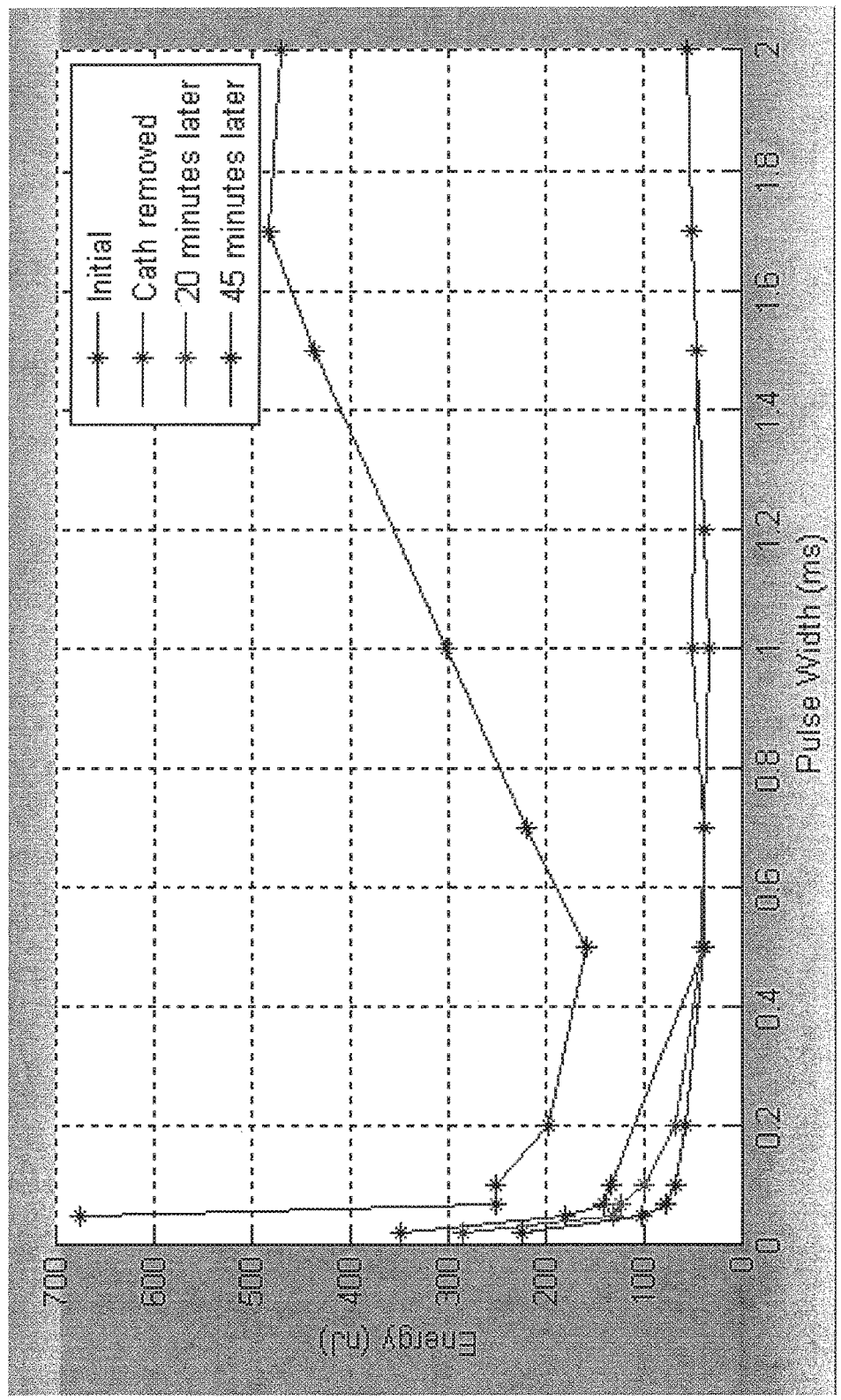
FIG. 1 is a graph illustrating the electrical energy needed to stimulate the tissue at different pulse widths taken at different times during an acute animal procedure.
Figure 2:
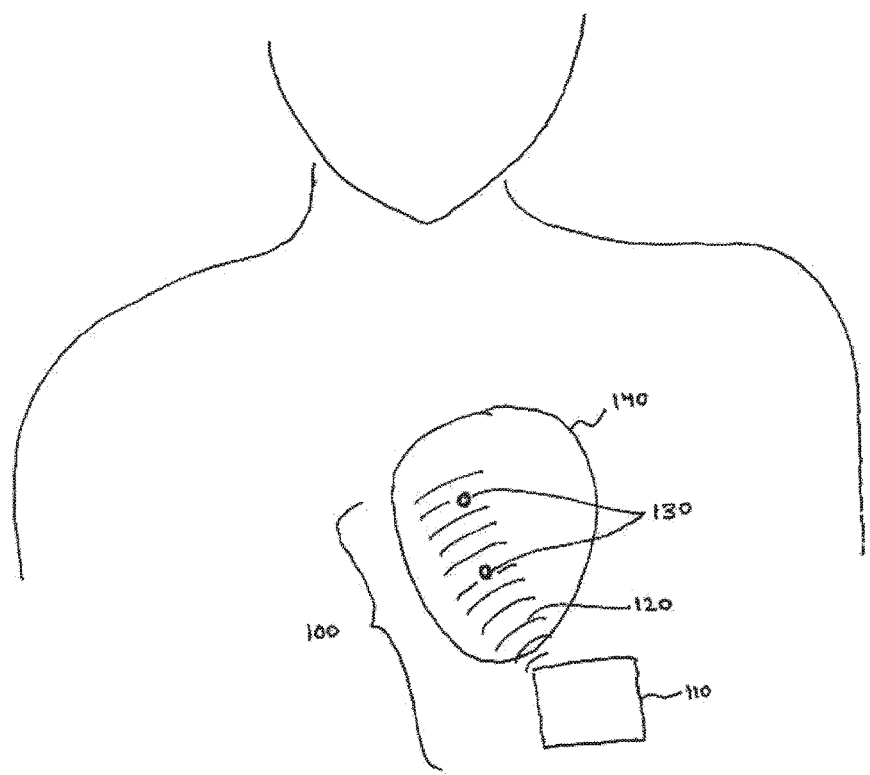
FIG. 2 is a block diagram illustrating a wireless tissue stimulation system configured to limit the electrical energy delivered to tissue to a level that does not stimulate tissue during diagnostic echocardiography.

As shown in FIG. 2, a wireless tissue stimulation system 100 comprises an implantable or external controller-transmitter (hereinafter also abbreviated as "C-T") 110 and one or more implantable receiver-stimulators 130 (hereinafter also abbreviated as "R-S"). C-T 110 generates acoustic energy 120 of sufficient amplitude and frequency to allow R-S 130 to generate electrical energy for tissue stimulation, and R-S 130 harvests and converts the acoustic energy into electrical energy and electrically stimulates tissue. The tissue is shown in FIG. 2 representatively as the heart, but it is understood that the tissue could be nerve tissue, brain tissue, muscle tissue, gastric tissue, bone tissue, and the like.

In one embodiment, the electrical energy sufficient to stimulate the heart is about 0.17 µJ for a 0.5 ms electrical pulse. This means that about 0.34 mW of power is delivered to the tissue during the 0.5 ms pacing pulse for sufficient stimulation of the heart.

The acoustic energy 120 propagates via an acoustic field whose acoustic intensity is defined as the amount of acoustic power passing through a cross-sectional area and can be expressed as Watts per square meter. The effective cross-sectional area of an R-S 130 is defined as the area available for harvesting acoustic energy. In one embodiment, the R-S 130 comprises an acoustic transducer assembly for converting acoustic energy into electrical energy. Ideally, the effective cross-sectional area of the R-S 130 would be the cross-sectional area of the R-S 130 that contains the acoustic transducer assembly. In practice, the effective area may be less than that, due to inefficiencies in harvesting and energy conversion. In one embodiment, the R-S 130 further comprises a tissue attachment mechanism and a catheter delivery interface. Due to the tissue attachment mechanism, catheter delivery interface, and other components of the R-S 130, the effective area may be substantially less than the cross sectional area of the R-S 130. In one embodiment, a 10 mm high R-S 130 has an estimated effective area of 2 mm$^2$=2·10$^{-6}$ m$^2$, which results in a minimum acoustic field of intensity of around $$\frac{0.34 \text{ mW}}{2 \cdot 10^{-6} \text{ m}^2} = \frac{170 \text{ W}}{\text{m}^2}$$

to stimulate the heart.

Figure 3:
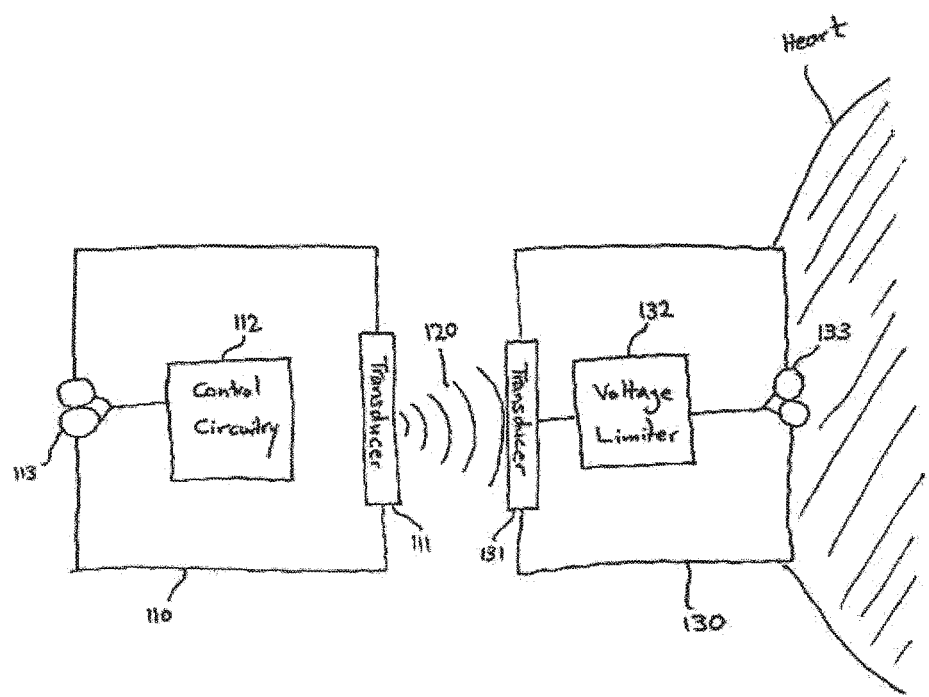
FIG. 3 is a block diagram showing the wireless tissue stimulation system in more detail.

The wireless tissue stimulation system is shown in more detail in FIG. 3. The C-T 110 comprises a control circuitry 112 and an output transducer assembly 111 for generating the acoustic energy 120 transmitted to the R-S 130. The transducer assembly 111 may be a single transducer, or may comprise multiple phased array transducers for steering and focusing acoustic energy on the R-S 130. The control circuitry 112 is configured to connect to a sensing electrode assembly 113. As described in further detail below, the sensing electrode assembly 113 is configured to sense or detect a spike voltage in the body caused by the voltage delivered to the tissue by R-S 130. Spike voltages occur due to the delivery of the electrical energy by the R-S 130 to the tissue. The control circuitry 112 of the C-T 110 selectively transmits acoustic pulses to generate query spike or pacing/stimulation spike voltages. The term query spike generally refers to pulses that are significantly shorter in duration than those used for pacing/stimulation. As described in more detail later, in this case query spikes are used to calibrate the output of the R-S 130. Similar short duration pulses may also be used to locate and focus acoustic energy for efficient transfer of acoustic energy to the R-S 130 as described in co-pending US Patent Publication No. 2008/0294208. It is envisioned that in a preferred embodiment query pulses are short enough to prevent tissue stimulation and also minimize energy consumption. In one embodiment, the sensing electrode assembly is disposed on the outer casing of the C-T 110. In another embodiment, the sensing electrode assembly 113 is connected to the C-T 110 via cables. Alternatively, the sensing electrode assembly 113 may be partly disposed on the outer casing of the C-T 110.

The R-S 130 comprises a piezoelectric receiving transducer assembly 131 capable of receiving acoustic energy 120 and converting the received acoustic energy into electrical energy. Optionally, the R-S 130 may comprise a rectifier component (not shown). The optional rectifier component is used to convert the electrical energy to an electrical output which can be configured to effectively stimulate the tissue (e.g., convert from AC electrical energy into a DC output, but other output waveforms are also effective).

In one embodiment, the electrical output of optional rectifier components are used to directly stimulate tissue. In an alternative embodiment, the R-S 130 further comprises processing circuitry that manipulates the electrical output converted by the rectifiers to produce an electrical signal that stimulates tissue. The processing circuitry manipulates the electrical output such that it is suitable for the particular stimulation application at hand, such as cardiac pacing, nerve stimulation, brain stimulation, voluntary muscle stimulation, pain amelioration, or the like. Such manipulation may involve summing or conditioning the electrical signals from the individual rectifiers to produce the biologically stimulating electrical output.

The R-S 130 also comprises a tissue contacting electrode assembly 133 capable of delivering an output voltage to stimulate the tissue. In one embodiment, the tissue contacting electrode assembly 133 comprises at least two stimulation electrodes in electrical contact with the tissue. Either or both of the stimulation electrodes may be mounted directly on the device, in some instances forming a portion of the R-S 130 casing, or extending from the R-S 130.

The R-S 130 further comprises a voltage limiter 132 configured to limit the output voltage delivered to tissue by the tissue contacting electrode assembly 133. In one embodiment, the voltage limiter 132 is placed within the contacting electrode assembly 133, such as between the stimulation electrodes. Alternatively, the voltage limiter 132 may be placed on the piezoelectric receiving transducer assembly 131, or anywhere between the receiving transducer assembly 131 and the tissue contacting electrode assembly 133, such that the voltage limiter 132 is able to limit the electrical voltage delivered to the tissue.

Figure 4:
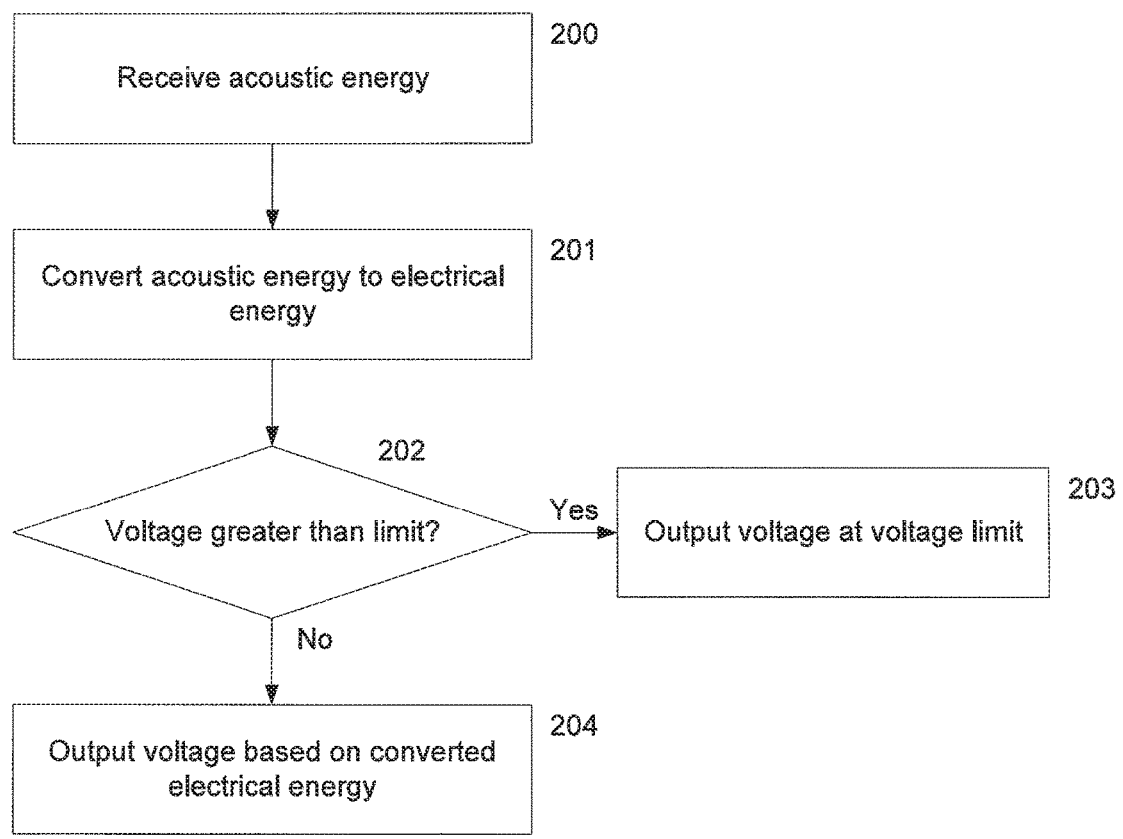
FIG. 4 is a flow diagram illustrating the operation of a receiver-stimulator configured to limit the electrical energy delivered to tissue to a level that does not stimulate tissue during diagnostic echocardiography.

FIG. 4 is a flow diagram illustrating the operation of the R-S 130, in accordance with an embodiment of the present invention. At step 200, the implantable R-S 130 wirelessly harvests or receives the acoustic energy 120 delivered from an acoustic source that is physically separate from the R-S 130, such as from the C-T 110. At step 201, the R-S 130 converts the received acoustic energy to electrical energy by the means of a piezoelectric receiving transducer assembly 131. Optionally, the R-S 130 then rectifies the electrical energy using a rectifier circuitry. At step 202, the electrical energy passes through a voltage limiter 132. When the voltage is at a level that is less than or equal to a maximum voltage limit as determined by the characteristics of the voltage limiter 132, then at step 204 the electrical voltage is delivered to the tissue by the tissue contacting electrode assembly 133. When the voltage is at a level that is greater than the maximum voltage limit, then at step 203 an electrical voltage corresponding to the maximum voltage limit is delivered to the tissue by the tissue contacting electrode assembly 133. Thereby, the voltage limiter 132 limits the electrical voltage delivered to the tissue.

Figure 5:
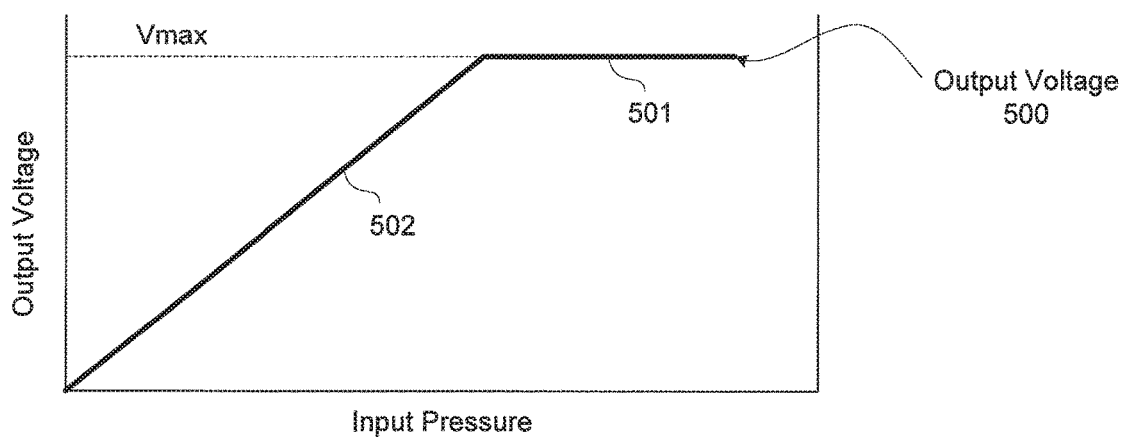
FIG. 5 is a graph illustrating a non-linear behavior or a voltage limiter.
Figure 6:
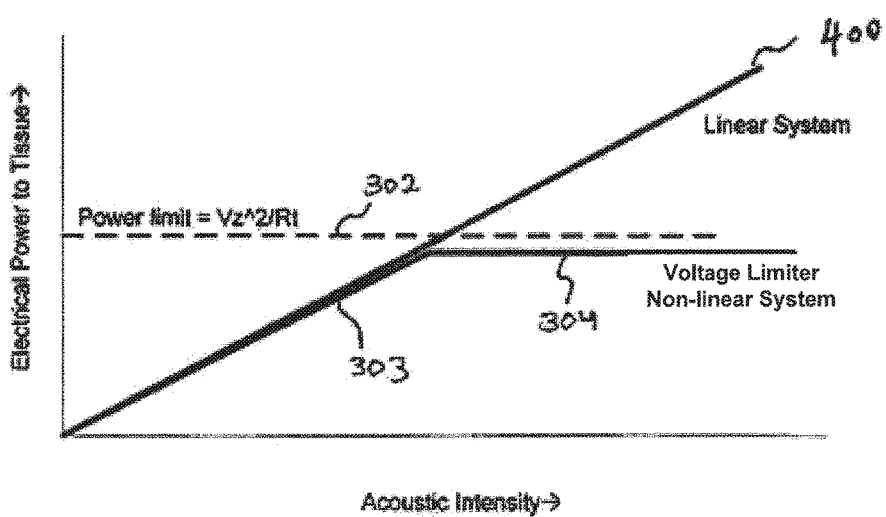
FIG. 6 is a graph illustrating a non-linear behavior of a wireless tissue stimulation system.

In a preferred embodiment, the present invention comprising the voltage limiter 132 is a non-linear system with respect to the amount of acoustic energy received by the R-S 130 and the electrical energy delivered to the tissue. FIG. 5 shows the behavior of the voltage limiter. The x axis is the input acoustic pressure which in a linear system is proportional to the output voltage of the device. The curve 500 has a linear portion 502, however for larger acoustic pressures the voltage limiter limits the output to a maximum output voltage resulting in a plateau 501 in the output voltage. Alternatively the relationship can be plotted in terms of acoustic intensity vs. output electrical power, as shown in FIG. 6. In a linear system 400, the output electrical power is proportional to the acoustic intensity or equivalently the square of the output voltage is proportional to the square of acoustic pressure. In this case the curve has similar linear 303 and non-linear 304 plateau regions, however the height of the plateau is replaced by the corresponding electrical power $$\frac{V_L^2}{R_t}$$

(where $V_L$ is the voltage limit and $R_t$ is the nominal tissue impedance, as also described below).

Once the electrical energy delivered to the tissue reaches a maximum output power 302, then the output voltage and hence electrical power delivered to the tissue 304 becomes independent of the acoustic intensity, in that an increase in acoustic intensity will not yield an increase in the electrical power delivered to the tissue. This is in contrast to a linear system, wherein the electrical power delivered to the tissue is in a linear relationship with the acoustic intensity, in that an increase in acoustic intensity yields an increase in electrical power delivered to the tissue throughout the input range of the acoustic intensity.

One advantage contemplated by the R-S 130 comprising a voltage limiter 132 is that the R-S 130 can function safely in the presence of interfering acoustic fields. The maximum output voltage 500 can be predetermined and configured to limit the electrical power delivered to the tissue to a level that does not stimulate tissue in the event that acoustic energy from acoustic fields generated by diagnostic acoustic imaging environments or other environments that generate significant acoustic fields are converted by the R-S 130 and delivered to the tissue. Limitations in the output voltage and in the pulse duration from these acoustic sources can be determined and R-S 130 configured such that electrical power delivered is not sufficient to stimulate the tissue, such as heart tissue.

According to one embodiment, the voltage limiter 132 is placed between the electrodes of the tissue contacting electrode assembly 133. The R-S 130 comprising a voltage limiter 132 will result in a non-linear system, as described above and in FIG. 4, with a maximum electrical power limit 302 of $$\frac{V_L^2}{R_t},$$

where $V_L$ is the voltage limit and $R_t$ is the nominal tissue impedance. For example, assuming an electrode-tissue impedance of approximately 1200 ohms, a voltage limiter with a voltage limit of about 3.6 V will limit the electrical power delivered to the tissue to about 10.8 mW.

In another embodiment, the voltage limit is about 2.24 V, which results in a maximum electrical power limit of 4.2 mW. The voltage limit may be set even lower for a greater safety margin.

It is contemplated that voltage limiters with various voltage limits may be utilized as the voltage limiter 132, depending on the intended usage of the R-S 130, such that the maximum electrical power limit as defined by the voltage limit is at least sufficient for the intended use. For example, a receiver-stimulator configured to stimulate nerve tissue may comprise a voltage limiter with a different voltage limit than a receiver-stimulator configured to stimulate cardiac tissue.

In one embodiment, the voltage limiter 132 may comprise a Zener diode. Alternatively, it is envisioned that the voltage limiter 132 may comprise elements or configurations other than a Zener diode for limiting the output voltage at a predetermined level independent of the received acoustic energy. For example, the voltage limiter may be one or more forward biased diodes placed in series.

Furthermore, the R-S 130 may comprise a low pass filter in addition to, or independent of, the voltage limiter 133. The low pass filter is configured to eliminate frequencies above a cutoff frequency while passing frequencies below the cutoff frequency. Thus, it is envisioned that the low pass filter may be utilized in the R-S 130 to eliminate acoustic energy transmitted to the tissue at a higher frequency than that of the desired acoustic source such as the C-T 110. For example, a typical operating frequency for an R-S 130 is in the range of 800 kHz to 1.3 MHz, while most acoustic diagnostic imaging systems operate at substantially higher frequencies in the range of 2-10 MHz. Thus, an R-S 130 comprising a low pass filter may prevent such acoustic energies of higher frequencies from interfering with the operation of the R-S 130. This low pass filter is applied to the output of the transducers prior to rectification. Alternatively, a low pass filter with a lower cutoff frequency can be applied in parallel with the voltage limiter, for example with a capacitor in parallel with the voltage limiter. The cutoff frequency is configured to be lower to allow the filter to reject short duration rectified pulses generated from diagnostic echo imaging while letting longer duration pacing pulses pass.

In another aspect, the present invention provides an implantable C-T 110 of a wireless stimulation system configured as a non-linear system as described above, wherein the C-T 110 is configured to estimate the output voltage of the R-S 130. To accomplish this, the C-T 110 is configured to sense a query spike voltage as described above in the tissue as a result of the output voltage delivered to the tissue by the R-S 130. Since the R-S 130 is configured to limit its output voltage, the C-T 110 is further configured to determine a maximum voltage when sensing such query spikes.

Once the maximum query spike voltage is determined, the C-T 110 determines a ratio of the maximum query spike voltage and the known, limited maximum output voltage of the R-S 130. This ratio allows the C-T 110 to determine or infer the output voltage of the R-S 130 based on a detected query spike voltage, when the output voltage is below the maximum and generally unknown.

Figure 7:
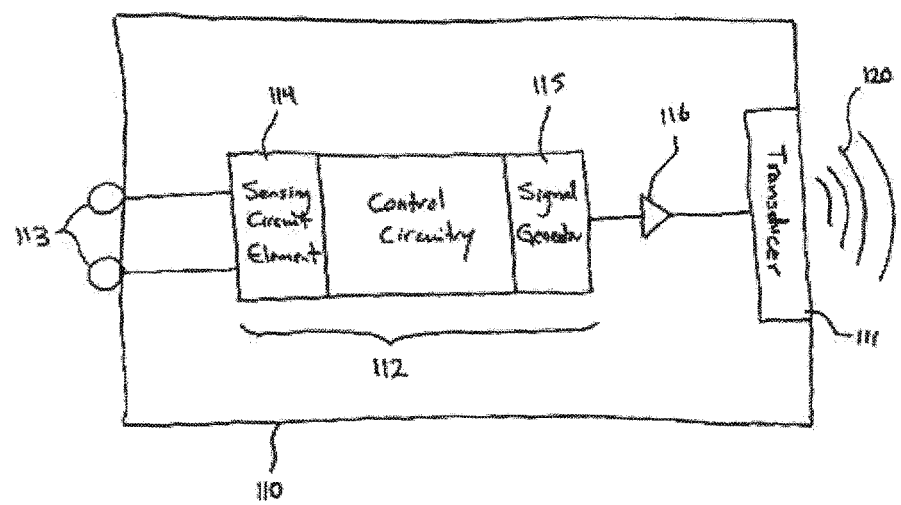
FIG. 7 is a block diagram illustrating a controller-transmitter configured to estimate the output voltage of a receiver-stimulator.

Referring now to FIG. 7, the C-T 110 comprises a power amplifier 116, an output transducer assembly 111, and a control circuitry 112 containing a signal generator 115 for generating and adjusting the acoustic energy 120 delivered to the R-S 130. The control circuitry 112 further comprises an electrical signal sensing circuit element 114 connected to the sensing electrode assembly 113. The sensing electrode assembly 113 is disposed on the outer casing of the C-T 110 or connected via cables to the C-T 110. Electrical signal sensing circuit element 114 may be an electrogram sensing circuit configured to amplify short duration pulses, or an electrical spike detection circuit. The sensing electrode assembly 113 and the signal sensing circuit element 114 are configured to sense or detect the query spike voltage in the body caused by the output voltage from the R-S 130. In one embodiment, the query spike voltage is detected at the chest near the rib cage. Alternatively, the query spike voltage may be detected at any other portion of the body. The control circuit 112 is configured to perform various processes, calculations, or estimations based on various detected or known parameters. In one embodiment, the control circuitry 112 is configured to process the detected query spike voltage information from the sensing circuit element 114.

Figure 8:
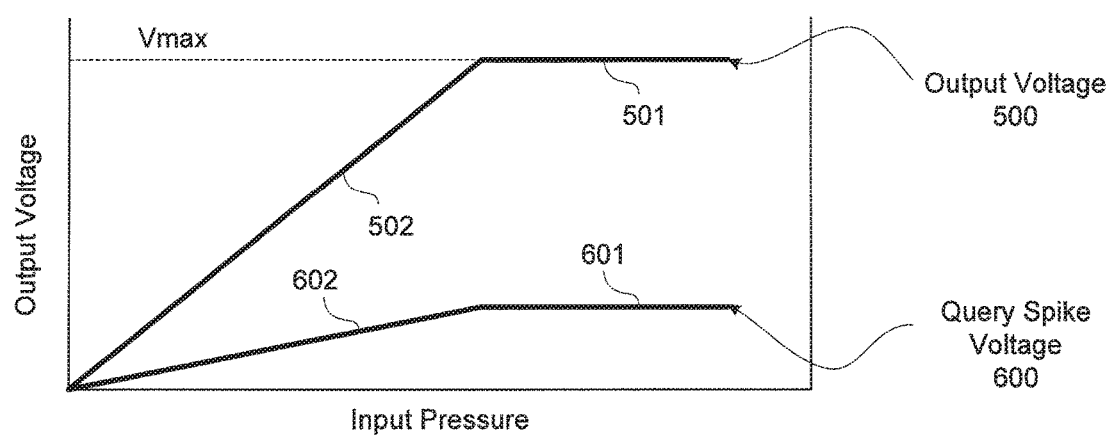
FIG. 8 is a graph illustrating a linear relationship between an output voltage of a receiver-stimulator and a query spike voltage detected by a controller-transmitter.

While the R-S 130 output voltage cannot be directly measured in a wireless stimulation system, in a non-linear system configuration as disclosed in the present invention, the C-T 110 is able to estimate the output voltage by remotely monitoring the query spike voltage caused by the output voltage from the R-S 130 delivered to the tissue. As seen in FIG. 8, the query spike voltage 600 is proportional to the output voltage 500 with a known maximum output voltage ($V_{max}$) 501. Thus, the C-T 110 is able to determine or infer the output voltage based on the measured query spike voltage 600 and the ratio between the output voltage 500 and the query spike voltage 600.

More specifically, the ratio between the query spike voltage 600 and the output voltage 500 is generally unknown and varies depending on the orientation of the R-S 130, distribution of the sensing electrodes 113 configured to detect the query spike voltage 600, and the distance between the R-S 130 and the sensing electrode assembly 113. However, given the non-linear behavior of the present invention, the ratio can be computed by the C-T 110 since the maximum output voltage 501 is predetermined by the characteristics of the voltage limiter 132 as described above.

Specifically, the maximum query spike voltage can be determined by the C-T 110 by monitoring the query spike voltage 600 until the query spike voltage plateaus and stops increasing despite further increases in the acoustic transmission. This is seen in FIG. 8 as the query spike voltage plateau 601. Since, as mentioned above, the query spike voltage 600, as detected by the C-T 110, is caused by the output voltage 500 of the R-S 130, the maximum query spike voltage as detected by the C-T 110 is caused by the maximum output voltage 501 of the R-S 130. Since both the maximum output voltage ($Max_{output}$) and the maximum query spike voltage ($Max_{pacing}$) can be determined, the control circuitry 112 can then calculate the ratio between the output voltage and the query spike voltage as $Max_{output}/Max_{pacing}$.

The C-T 110 is thus able to determine or infer the output voltage 502 even when the output voltage is not at the maximum, using the computed voltage ratio and the detected query spike voltage 602.

Figure 9:
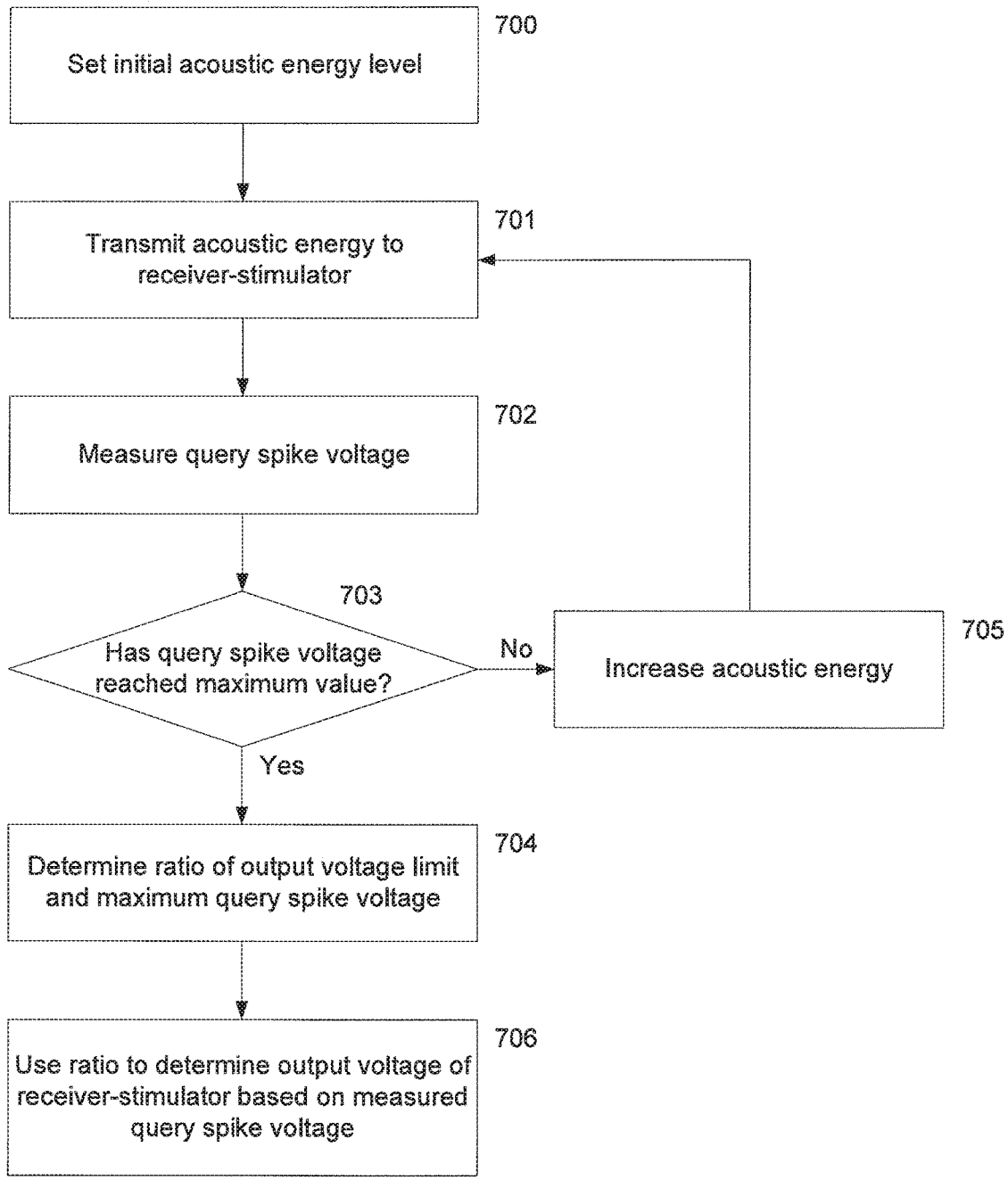
FIG. 9 is a flow diagram illustrating the operation of a controller-transmitter configured to estimate the output voltage of a receiver-stimulator.

FIG. 9 illustrates a flow diagram of an exemplary operation of the C-T 110 to determine or infer the output voltage. At step 700, the control circuitry 112 of the C-T 110 is first configured to set the initial amount of acoustic energy to be transmitted into the tissue. At step 701, the signal generator 115, the power amplifier 116, and the transducer assembly 111 are configured to deliver the acoustic energy 120 to the R-S 130. The R-S 130 then converts the acoustic energy into electrical energy, which is then delivered to the tissue. At step 702, the sensing circuit element 114 measures the query spike voltage in the tissue as a result of the output voltage delivered into the tissue by the R-S 130.

At step 703, the control circuitry 112 determines whether the query spike voltage has reached a maximum value, as described above. If the query spike voltage has indeed reached a maximum value, at step 704 the control circuitry 112 calculates the ratio of maximum electrical energy limit and the maximum query spike voltage. Subsequently, at step 706, the control circuitry 112 uses the calculated ratio of maximum electrical energy limit and the maximum query spike voltage to estimate the output voltage of the R-S 130 based on the measured query spike voltage.

However, if at step 703 the control circuitry 112 determines that the query spike voltage has not yet reached a maximum value, then at step 705 the C-T 110 will increase the acoustic energy level to be transmitted and return to step 701 to deliver the increased acoustic energy 120 to the R-S 130. The operation loop described above will continue until the C-T 110 determines that a maximum spike voltage value has been reached.

In actual practice, the controller-transmitter must be calibrated to take into account that the voltage limiter in the receiver-stimulator may not function as a perfect switch. Therefore, the query spike voltage will continue to increase, albeit at a much lower rate even after the output voltage has reached the maximum voltage limit. Additionally, both the controller-transmitter and the receiver-stimulator move dynamically during operation in an in vivo environment. Indeed, the dynamic motion in an in vivo environment can easily change the targeting accuracy of the controller-transmitter over the course of a cardiac or respiratory cycle. Therefore, in practice it is desirable that the output voltage, as generated by the R-S 130, vary dynamically depending on the location of the C-T 110. Thus, it is desirable that the calibration be done rapidly with a minimal number of queries and with minimal delay between output calibration and transmission of a pacing pulse.

An Exemplary Implementation

The following illustrates an example implementation for determining or inferring the output voltage of a receiver-stimulator using a controller-transmitter in an in vivo environment. The example is provided as illustration and should not be construed as limiting.

Figure 10:
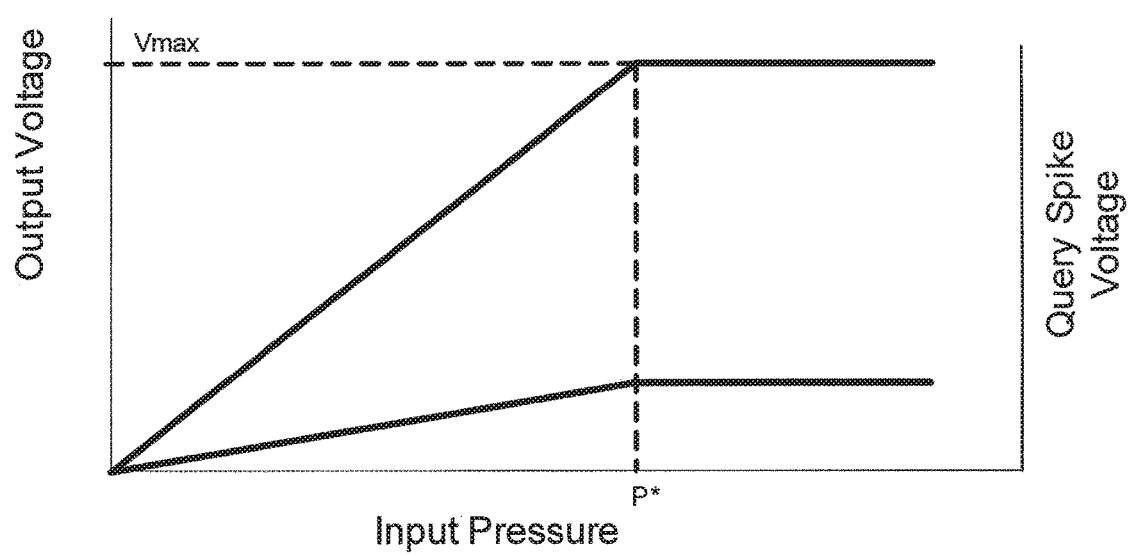
FIGS. 10-12 illustrate an exemplary implementation of the present techniques.

As described above, the controller-transmitter varies the transmitted acoustic energy while monitoring the query spike voltage to determine the level of acoustic energy for which the query spike voltage stops increasing, shown as p* in FIG. 10 illustrating an ideal transfer function, and equating this with an output $Max_{output}$ of the receiver-stimulator. In practice, this calibration procedure would use a very short duration query spike that is not stimulating and that minimizes energy consumption. In one embodiment, a preferred duration for query spikes is in the range of about 10 μs-100 μs, as opposed to pacing pulses which are in the range of about 100 μs-2 ms.

Once p* is known, an output voltage $v < V_{max}$ can be achieved by applying an input pressure $$p(v) = \frac{v}{V_{max}} p^*.$$

In practice, there are several factors that are considered when calibrating the receiver-stimulator output to determine p*, namely (1) that the output limiter in the receiver-stimulator is generally not an ideal switch as shown in FIG. 5, and (2) that the controller-transmitter and the receiver-stimulator are moving dynamically and relative to each other. Therefore, the calibration is done rapidly with a minimal number of queries and with a minimal delay between output calibration and transmission of a pacing pulse.

Figure 11:
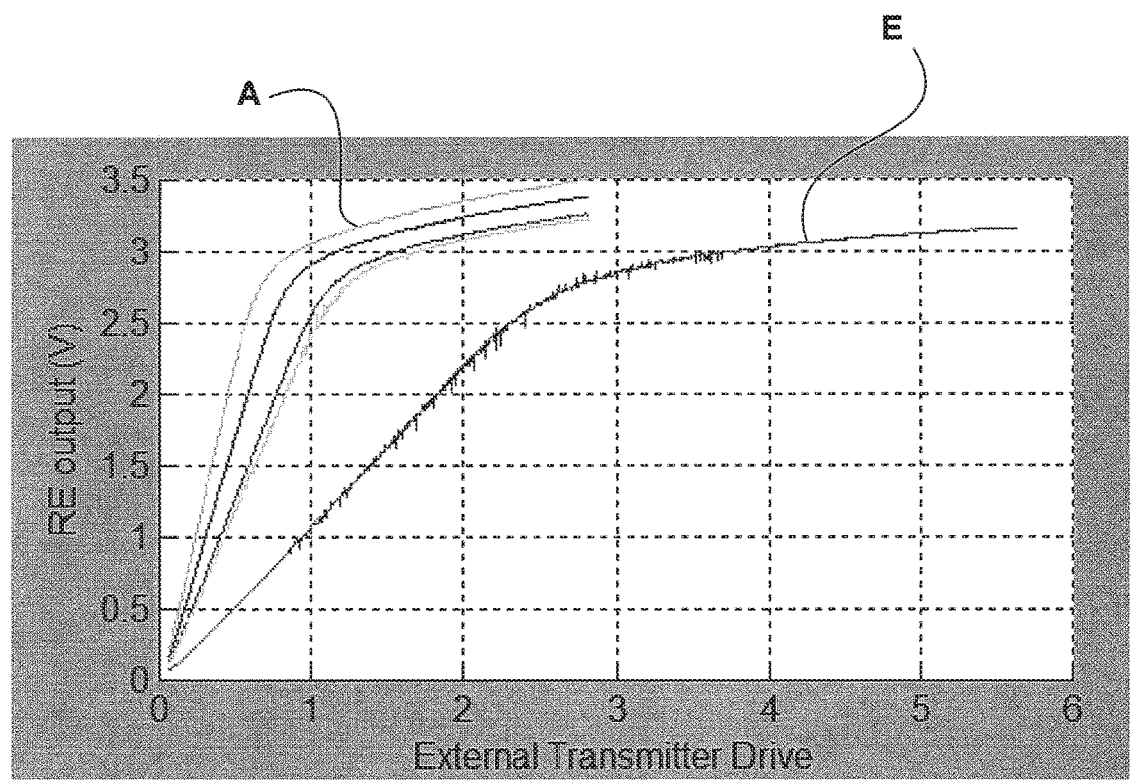

FIG. 11 shows exemplary bench measurements of receiver-stimulator transfer functions. The horizontal axis represents the voltage used to drive the controller-transmitter, which is proportional to the acoustic pressure transmitted by the controller-transmitter. The vertical axis represents the output of the receiver-stimulator. The different curves reflect different degrees of targeting, starting with curve A on the left which is perfectly targeted, to curve E on the right which reflects poor targeting. Perfect targeting means that the peak of the acoustic field produced by the controller-transmitter is at the location of the receiver-stimulator. The targeting was degraded by simply moving the controller-transmitter laterally away from the location that produced the best acoustic transfer to the receiver-stimulator (perfect targeting).

Since dynamic motion in an in vivo environment can easily change the targeting accuracy over the course of a cardiac or respiratory cycle, in practice the receiver-stimulator transfer function can change dynamically from one curve in FIG. 11 to another. Therefore, as mentioned above, it is important for the calibration algorithm to execute rapidly, thereby effectively freezing such motion.

Another aspect of the transfer functions shown in FIG. 11 is that the receiver-stimulator output is not flat for large external controller-transmitter drive levels. This is caused by the non-ideal nature of the voltage limiter, which is generally not a perfect switch. Accordingly, the output of the receiver-stimulator continues to climb, albeit at a much lower rate.

Note that the curves in FIG. 11 have a similar shape and differ by a scaling of the horizontal axis. Accordingly, the control algorithm can be developed by starting with one of these curves. This is labeled in FIG. 12 as F(x), wherein x is the controller-transmitter drive voltage. We define a new function $$G(x) \equiv \frac{F(\alpha x)}{F(x)},$$

$$\alpha < 1$$

wherein x is the output voltage of the receiver-stimulator F(x) is the measured query spike voltage, and α is the factor of decrease in acoustic energy level.

Because G(x) is a ratio of two measured query spike voltages, it has the desirable property that it is identical whether F(x) is the actual receiver-stimulator output or a scaled measurement thereof, such as a remote measurement of the output using a surface electrogram at the controller-transmitter location.

Figure 12:
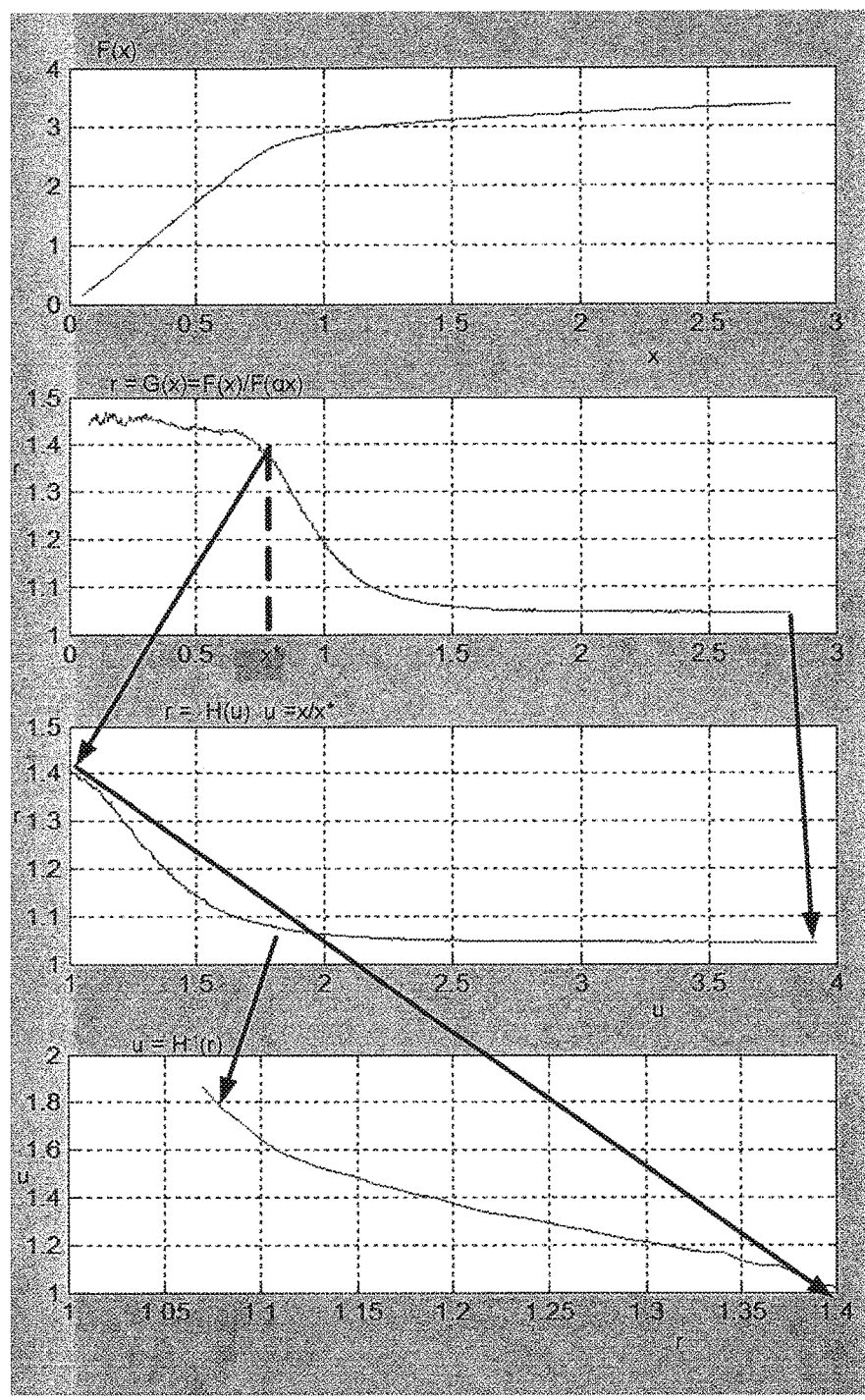

Referring now to the graphs of FIG. 12, F(x) and G(x) are shown in the first two graphs, with G(x) shown exemplarily with $$\alpha = \frac{1}{\sqrt{2}} \approx 0.707.$$

For drive voltages in the linear region of the receiver-stimulator, $$x < x^* \text{ and } G(x) \approx \frac{1}{\alpha}.$$

For $x \geq x^*$, the output of the receiver-stimulator is limited and $G(x) \rightarrow 1$.

Next we apply the variable transformation $$u = \frac{x}{x^*}$$

and define the function $r=H(u) \equiv G(ux^*)$ for $u>1$ as shown in the third graph of FIG. 12.

Finally we can define the inverse of this function $u=H^{-1}(r)$ as long as $r=H(u)$ is one to one. Therefore, we can compute $u=H^{-1}(r)$ for $1.4>r>1.08$. This is shown in the last graph in FIG. 12.

An exemplarily implementation of the calibration algorithm by the controller-transmitter using functions and variables defined above is as follows:

Control Algorithm $x_n$ is the transmit voltage at the $n^{th}$ algorithm step, with $x_0$ representing the initial transmit voltage. One iteration of the calibration algorithm comprises the following steps:
1. Measure response $F(x_n)$
2. Decrease drive voltage by $\alpha$ and measure response $F(\alpha x_n)$ 3. Compute $r = \dfrac{F(x_n)}{F(\alpha x_n)}$ 4. Depending on the value of r compute $x^*$, and $x_{n+1}$, the drive voltage for the next iteration step, as:

$$r > \frac{0.95}{\alpha}$$
$x^*$ undefined
$$x_{n+1} = \frac{x_n}{\alpha}$$
$$\frac{0.95}{\alpha} \geq r > 1.08$$
$$x^* = \frac{x_n}{H^{-1}(r)}$$
$$x_{n+1} = \frac{x_n}{\alpha H^{-1}(r)} = \frac{x^*}{\alpha}$$
$1.08 \geq r$ $x^*$ undefined
$$x_{n+1} = \alpha x_n$$

The control algorithm iterates until the middle criteria for r is met, i.e.

$$\frac{0.95}{\alpha} \geq r > 1.08,$$

at which point the inflection point x* is known and the control algorithm has calibrated the acoustic transfer from the controller-transmitter to the receiver-stimulator. A specific output voltage $V_{out}$ for the receiver-stimulator can be achieved by setting the drive voltage to $$x = x^* \frac{V_{out}}{V_{out}(x^*)},$$

wherein $V_{out}(x^*)$ is the output of the receiver-stimulator at the inflection point x* which, for the receiver-stimulator data shown in FIG. 12, is approximately 2.8V.

While the above is a complete description of the preferred embodiments of the invention, various alternatives, modifications, and equivalents may be used. Therefore, the above description should not be taken as limiting the scope of the invention which is defined by the appended claims.

What is claimed is:

1. An implantable medical device system for delivering electrical stimulation pulses to a patient, comprising:
   a controller-transmitter defining a first implantable device having an output transducer assembly and control circuitry, wherein the control circuitry is configured to control the output transducer assembly to transmit a first acoustic energy at an electrical pulse rate configured to electrically pace/stimulate cardiac tissue; and
   a receiver-stimulator defining a second implantable device having a piezoelectric receiving transducer configured to receive the first acoustic energy from the controller-transmitter and a second acoustic energy from a diagnostic ultrasound source and convert it to an electrical output, a circuit coupled to the piezoelectric receiving transducer to receive the electrical output and produce an output energy, and electrodes electrically coupled to the circuit and configured to deliver the output energy to pace/stimulate the cardiac tissue, wherein the circuit is configured to produce the output energy by —
   (a) delivering to the electrodes a first portion of the electrical output produced by the piezoelectric receiving transducer in response to the first acoustic energy transmitted by the controller-transmitter, and
   (b) filtering out a second portion of the electrical output produced by the piezoelectric receiving transducer in response to the second acoustic energy produced by the diagnostic ultrasound source.

2. The system of claim 1 wherein the output transducer assembly comprises multiple phased array transducers configured to steer and focus the first acoustic energy.

3. The system of claim 1 wherein the circuit of the receiver-stimulator comprises a low pass filter configured to eliminate voltage associated with the second acoustic energy produced by the diagnostic ultrasound source.

4. The system of claim 1 wherein the circuit of the receiver-stimulator comprises a low pass filter configured to provide electrical energy to the electrodes associated with the first acoustic energy in the range of 800 kHz to 1,3 MHz while filtering out electrical energy associated with the second acoustic energy in the range of 2 MHz to 10 MHz.

5. An implantable medical device system for delivering electrical stimulation pulses to a patient, comprising:
   a controller-transmitter defining a first implantable device having an output transducer assembly and control circuitry, wherein the control circuitry is configured to control the output transducer assembly to transmit a first acoustic energy configured to electrically pace/stimulate cardiac tissue; and
   a receiver-stimulator defining a second implantable device having a piezoelectric receiving transducer configured to receive the first acoustic energy from the controller-transmitter and a second acoustic energy from a diagnostic ultrasound source and convert it to an electrical output, a circuit coupled to the piezoelectric receiving transducer to receive the electrical output and produce an output energy, and electrodes electrically coupled to the circuit and configured to deliver the output energy to pace/stimulate the cardiac tissue, wherein the circuit is configured to produce the output energy by —
   (a) delivering to the electrodes a first portion of the electrical output produced by the piezoelectric receiving transducer in response to the first acoustic energy transmitted by the controller-transmitter, and
   (b) preventing a second portion of the electrical output produced by the piezoelectric receiving transducer in response to the second acoustic energy produced by the diagnostic ultrasound source from being delivered to the electrodes.

6. The system of claim 5 wherein the output transducer assembly comprises multiple phased array transducers configured to steer and focus the first acoustic energy.

7. The system of claim 5 wherein the circuit of the receiver-stimulator comprises a low pass filter configured to eliminate voltage associated with the second acoustic energy produced by the diagnostic ultrasound source.

8. The system of claim 5 wherein the circuit of the receiver-stimulator comprises a low pass filter configured to provide electrical energy to the electrodes associated with the first acoustic energy in the range of 800 kHz to 1.3 MHz while filtering out electrical energy associated with the second acoustic energy in the range of 2 MHz to 10 MHz.

* * * * *

UNITED STATES PATENT AND TRADEMARK OFFICE
CERTIFICATE OF CORRECTION

PATENT NO. : 10,512,785 B2
APPLICATION NO. : 16/250943
DATED : December 24, 2019
INVENTOR(S) : Moore et al.

Page 1 of 1

It is certified that error appears in the above-identified patent and that said Letters Patent is hereby corrected as shown below:

On the Title Page

Item (54) and in the Specification, Column 1, Line 1, delete "ACCOUSTIC" and insert -- ACOUSTIC --, therefor.

In the Claims

In Column 15, Line 6, in Claim 4, delete "1,3" and insert -- 1.3 --, therefor.

Signed and Sealed this
Fifteenth Day of February, 2022

Drew Hirshfeld
*Performing the Functions and Duties of the*
*Under Secretary of Commerce for Intellectual Property and*
*Director of the United States Patent and Trademark Office*